United States Patent [19]
Snyder et al.

[11] Patent Number: 6,117,218
[45] Date of Patent: Sep. 12, 2000

[54] SCENTING DEVICE FOR HVAC SYSTEMS

[75] Inventors: Michael R. Snyder, Shawnee, Kans.; Gary A. Robinson, Amherst, N.Y.

[73] Assignee: Web Products, Inc., Kansas City, Kans.

[21] Appl. No.: 09/234,739

[22] Filed: Jan. 21, 1999

Related U.S. Application Data
[60] Provisional application No. 60/081,358, Apr. 10, 1998.

[51] Int. Cl.[7] .................................................. A61L 9/04
[52] U.S. Cl. ........................... 96/222; 428/905; 422/123; 261/DIG. 17
[58] Field of Search ............................... 96/222; 428/905; 422/123, 124; 239/60; 523/102; 261/DIG. 17, 100; 55/DIG. 35

[56] References Cited

U.S. PATENT DOCUMENTS

| | | | |
|---|---|---|---|
| 3,685,734 | 8/1972 | Paciorek et al. | 239/56 |
| 3,804,796 | 4/1974 | Alexandre | 260/42.43 |
| 3,902,877 | 9/1975 | Swaim | 220/306 |
| 4,065,262 | 12/1977 | Petroff | 21/74 R |
| 4,095,031 | 6/1978 | Engle | 526/1 |
| 4,118,226 | 10/1978 | Bourassa | 55/279 |
| 4,285,468 | 8/1981 | Hyman | 239/55 |
| 4,346,840 | 8/1982 | Gaiser et al. | 239/6 |
| 4,383,377 | 5/1983 | Crafton | 34/60 |
| 4,425,321 | 1/1984 | Jacquet et al. | 424/47 |
| 4,515,909 | 5/1985 | Sawano et al. | 523/102 |
| 4,517,308 | 5/1985 | Ehlenz et al. | 502/401 |
| 4,563,333 | 1/1986 | Frigon | 422/122 |
| 4,604,114 | 8/1986 | Ward | 55/279 |
| 4,676,954 | 6/1987 | Wilson | 422/124 |
| 4,695,434 | 9/1987 | Spector | 422/116 |
| 4,696,844 | 9/1987 | Spector | 428/46 |
| 4,720,409 | 1/1988 | Spector | 428/46 |
| 4,735,358 | 4/1988 | Morita et al. | 239/1 |
| 4,741,944 | 5/1988 | Jackson et al. | 428/152 |
| 4,761,437 | 8/1988 | Christie | 523/102 |
| 4,809,912 | 3/1989 | Santini | 239/60 |
| 4,857,240 | 8/1989 | Kearnes et al. | 261/26 |
| 4,903,583 | 2/1990 | Frazier | 98/30 |
| 4,959,087 | 9/1990 | Kappernaros | 239/60 |
| 4,960,240 | 10/1990 | McElfresh | 239/56 |
| 5,019,434 | 5/1991 | Matsumoto | 428/35.7 |
| 5,034,222 | 7/1991 | Kellett et al. | 424/76.4 |
| 5,087,273 | 2/1992 | Ward | 55/279 |
| 5,109,029 | 4/1992 | Malone | 521/79 |
| 5,163,616 | 11/1992 | Bernarducci et al. | 239/35 |
| 5,240,653 | 8/1993 | Ramkissoon | 261/99 |
| 5,242,521 | 9/1993 | Hibsch et al. | 156/200 |
| 5,250,265 | 10/1993 | Kawaguchi et al. | 422/107 |
| 5,258,051 | 11/1993 | Anderson | 55/279 |
| 5,273,690 | 12/1993 | McDowell | 428/905 |
| 5,314,669 | 5/1994 | Hamilton | 422/305 |
| 5,527,493 | 6/1996 | McElfresh et al. | 261/30 |
| 5,556,030 | 9/1996 | Paul | 239/56 |
| 5,611,486 | 3/1997 | Paul | 239/56 |
| 5,698,166 | 12/1997 | Vick et al. | 428/905 |
| 5,780,527 | 7/1998 | O'Leary | 523/102 |
| 5,782,409 | 7/1998 | Paul | 239/56 |
| 5,833,971 | 11/1998 | Baldwin | 424/76.4 |

*Primary Examiner*—David A. Simmons
*Assistant Examiner*—Frank M. Lawrence
*Attorney, Agent, or Firm*—Woodcock Washburn Kurtz Mackiewicz & Norris LLP

[57] ABSTRACT

A scenting device for attachment to an air filter in a HVAC system. The scenting device comprises a sheet formed from a material that is substantially impervious to air. The sheet is cut so as to form at least one opening through which the air to be scented flows. The opening is preferably serpentine and defines a plurality of fingers in the sheet. A relatively thick layer of a high viscosity liquid, such as a gel, containing a fragrance is deposited onto the sheet. The device is made by partially cutting through the sheet so as to form a zone of weakness having the shape of the intended opening. After the fragrance-containing material is deposited on the sheet, it is packaged and slipped to the user. The user tears the sheet along the zone of weakness, thereby forming the opening.

9 Claims, 3 Drawing Sheets

SCENTING DEVICE FOR HVAC SYSTEMS

RELATED APPLICATIONS

This application claims the benefit of U.S. Provisional Application No. 60/081,358, filed on Apr. 10, 1998, hereby incorporated by reference as if set forth fully herein.

BACKGROUND OF THE INVENTION

This invention relates to improvements in air freshening devices such as those used in forced-air heating, ventilating and air conditioning (HVAC) systems and, in particular, to a scented attachment for an air filter which is convenient for the user to handle and affix to the filter, and which has an extended useful life.

Various air freshening or scenting devices have been proposed for imparting a desired fragrance to the air in homes and offices by interposing a fragrant material in the airstream of a HVAC system. Several devices of this type are currently available in the marketplace and generally consist of a piece of foam rubber or similar substrate which holds a fragrant material, typically in the form of a solid residue, on its surface and/or in the pores of the foam. A desired scent is imparted to the air as it passes through the foam and contacts the fragrant material.

Although these devices have been commercially successful, they present certain important disadvantages. First, the useful life of the fragrant material may be insufficient to impart a significant useful life to the device, requiring that a used device be discarded and a fresh one attached to the filter at frequent intervals if the fragrance is to be maintained. Additionally, the foam rubber is often wet or greasy to the touch and is not pleasant to handle and install.

SUMMARY OF THE INVENTION

It is, therefore, the primary object of the present invention to provide an air scenting device for HVAC systems which has a long useful life and is convenient and pleasant to handle and install on an air filter.

This and other objects is accomplished in a scenting device for attachment to a filter through which air flows. The device comprises (i) a substantially planar substrate that has first and second faces on its opposing sides and in which at least one air passage formed, (ii) a layer of fragrance-containing gel adhered to and covering a portion of a face of the substrate, and (iii) a connector for attaching the sheet to the air filter so as to impart a desired scent to the air flowing therethrough. In a preferred embodiment of the invention, the substrate is formed from a substantially air impermeable material, and the air passage formed in the substrate extends between the faces and forms at least one pair of spaced, side-by-side segments defining at least one finger on which the fragrance-containing gel is deposited. Such passage may be formed by creating a zone of weakness in the substrate that allows it to be torn so as to create the desired shape passage prior to use by the user. In addition, the room temperature viscosity of the fragrance-containing gel is sufficiently great so as to form a layer containing at least approximately 0.06 cubic inches of the fragrance-containing gel for each square inch of the substrate covered by the gel layer.

The current invention also encompasses a method of making a scenting device for attachment to a filter through which air flows, comprising the steps of (i) forming a substantially planar substrate, the substrate having first and second faces on opposing sides thereof, (ii) forming a zone of weakness in the substrate so as to allow a portion of the substrate to be torn therefrom so as to create at least one opening having a predetermined shape, (d) depositing a layer of heated, fragrance-containing gel onto the substrate, the layer of fragrance-containing gel covering a portion of the substrate first face, and (e) cooling said gel so that it forms a relatively thick layer on the substrate.

DETAILED DESCRIPTION OF THE PREFERRED EMBODIMENT

Figure 1:
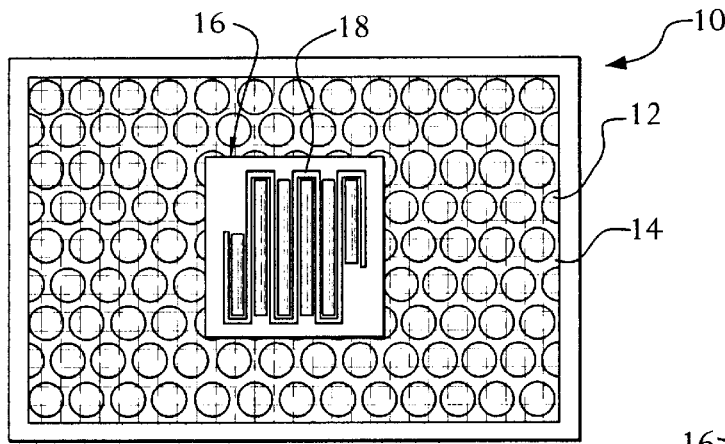
FIG. 1 is a front elevation view of a disposable furnace filter of a conventional type, showing the scenting device of the present invention mounted on the upstream face of the filter.
Figure 2:
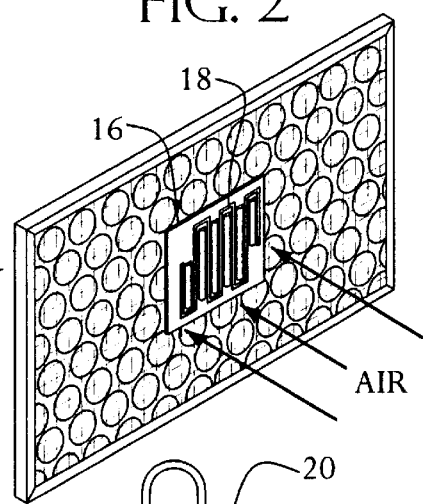
FIG. 2 is a perspective view of the filter of FIG. 1 showing the scenting device thereon and illustrating the direction of the airflow with arrows.
Figure 4:
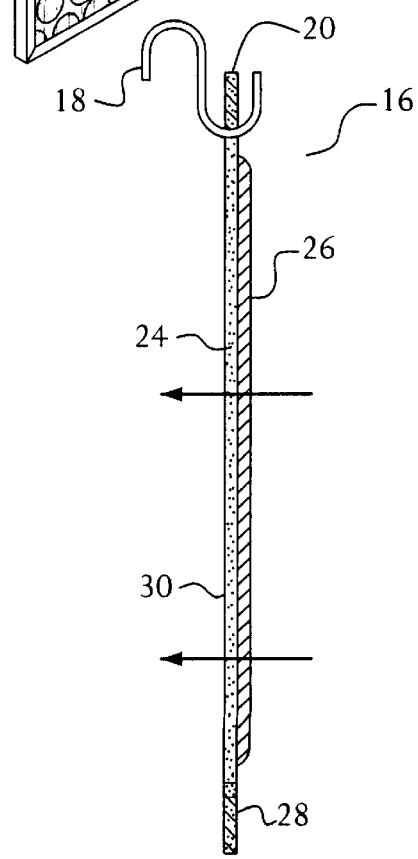
FIG. 4 is a cross-sectional view of the device taken along line 4—4 in FIG. 3.

Referring initially to FIGS. 1 and 2, a conventional disposable furnace filter 10 is illustrated and is of the type that a consumer typically obtains from a hardware store or other retail outlet. A filter medium 12 is held within the rectangular frame of the filter and may include a formations sheet 14 to increase the rigidity of the filter assembly. Air filters of this type readily support the device of the present invention shown at 16 secured to the upstream face of the filter 10 by a simple connector such as an S-hook 18, shown best in FIG. 4. Other connectors, such as pins, barbs, clips, clamps, tape, adhesives, etc. could also be utilized It should be understood that although a disposable air filter 10 is illustrated, the device 16 of the present invention may be used with permanent HVAC filter assemblies that provide an upstream face to which the device 16 may be attached.

Figure 3:
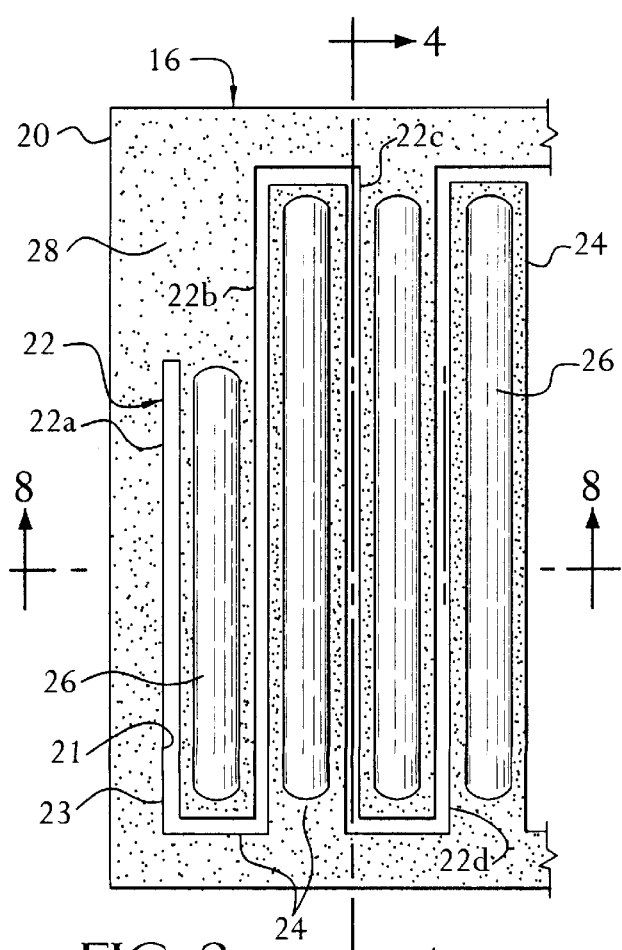
FIG. 3 is an enlarged, fragmentary view of the scenting device shown in FIG. 1 removed from the filter.

As shown best in FIG. 3, the device 16 comprises a sheet 20 having an approximately square shape. The sheet 20 provides a substrate or support for the fragrant substance, as discussed below, and is preferably formed from substantially air-impermeable material. Most preferably, the sheet 20 is formed from blotter paper having a thickness of about 0.07 inch. Blotter paper, formed by compressing a blend of pulps into a sheet, is dense and thus presents a relatively rigid backing. It should be appreciated, however, that other substrates could also be used if desired. The size of sheet 20 should be approximately six to seven inches square for typical HVAC systems.

Preferably a single sinuous, or serpentine, opening 22 is formed in the sheet 20 so as to define a plurality of parallel fingers 24. Each of the fingers 24 supports an elongated layer or strip of a fragrance-containing substance 26 that is deposited on, and adheres to, the upstream face 28 of sheet 20. It will be appreciated that the downstream face 30 of sheet, shown in FIG. 4, will contact and be held against the upstream face of the furnace filter 10 when the device 16 is mounted thereon by the hook 18.

The opening 22 provides a passage through which the air to be scented flows, thereby exposing it to the strips of fragrance-containing substance 26. In the preferred embodiment shown, the sinuous opening 22 presents a plurality of spaced, straight, parallel, side-by-side segments, four of such segments being denoted 22a, 22b, 22c and 22d in the fragmentary view of FIG. 3. It will be appreciated that the opening 22 consists of seven successive segments in the illustrated embodiment. These segments define six fingers 24 in the sheet 20, each of which supports one of the strips of fragrance-containing substance 26 on its upstream face. It should be understood that a greater or lesser number of fingers 24 and corresponding fragrant strips of fragrance-containing substance 26 may be utilized if desired. As shown best in FIGS. 3 and 4, each of the strips 26 is spaced inwardly from the edges 21, 23 of the opening 22 that defines the finger on which it is deposited.

Figure 7:
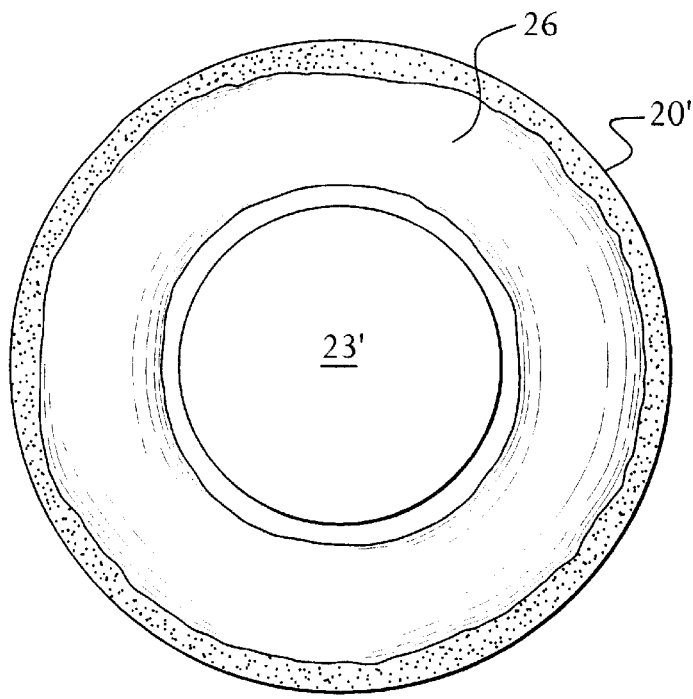
FIG. 7 is a view of a fourth embodiment of the scenting device according to the current invention.
Figures 5, 6:
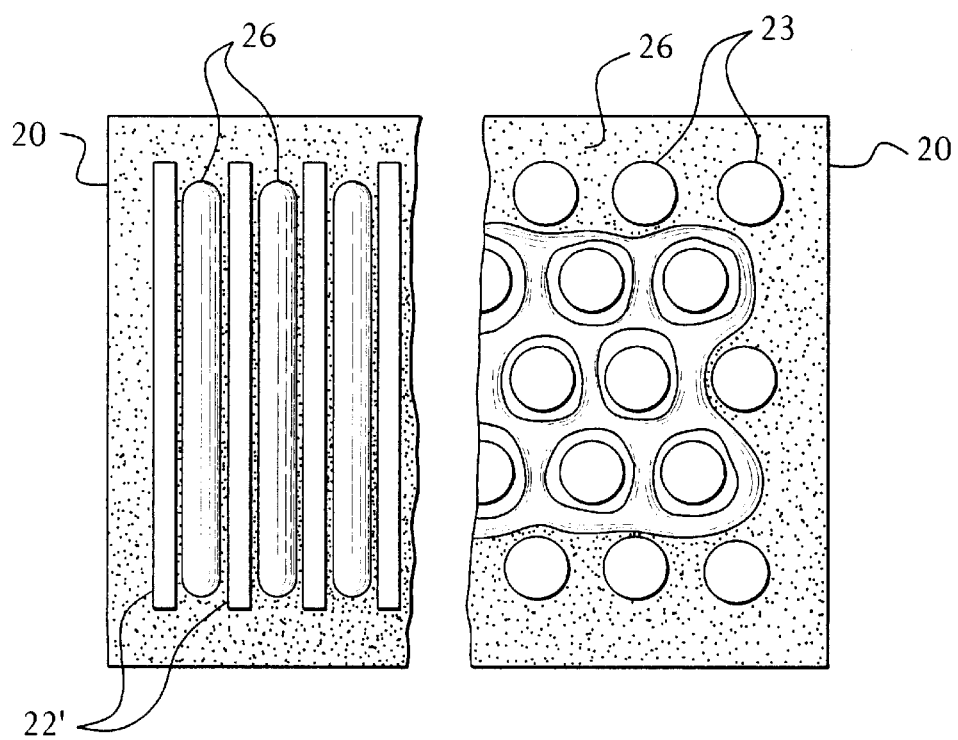
FIG. 5 is a fragmentary view of a second embodiment of the scenting device according to the current invention.
FIG. 6 is a fragmentary view of a third embodiment of the scenting device according to the current invention.

The shape of the sheet, as well as the shape and number of openings in the sheet, can be varied according to the current invention. For example, FIG. 5 shows an alternate embodiment of the invention in which the single sinuous opening 22 is replaced by a number of parallel elongate openings 22'. Strips of the fragrance-containing substance 26 are deposited on the upstream face of the sheet 20 between each of the openings 22'. FIG. 6 shows an embodiment in which the elongate openings 22' are replaced by holes 23. In this embodiment. the fragrance-containing substance 26 is disposed between and around the holes 23. FIG. 7 shows an embodiment in which the sheet 20' is circular and features a single circular opening 23. A donut shaped strip of fragrance-containing substance 26 surrounds the circular opening 23'.

As used herein, the term "net surface area" of the sheet 20 refers to the surface area of only the material forming the sheet, calculated by subtracting the surface area of the opening from the surface area based on the outside dimensions of the sheet. Thus, if the sheet 20 is 5 inches square and has a single 2 inch square opening formed in it (i.e., a flow area of 4 square inches), the net surface area would be 21 square inches.

The larger the net surface area of the sheet 20, the larger the volume of fragrance-containing material 26 that can be deposited onto the sheet and, consequently, the more effective the release of fragrance. However, due to the air impervious nature of the material from which the sheet 20 is formed, the use of an air freshener with too large a net surface area could create excessive resistance to flow in the air circulation system, resulting in excessive pressure drop and an inadequate air flow rate.

According to the current invention, this problem is solved by employing a fragrance-containing material 26 that has a very high viscosity at room temperature, such as a gel. The high viscosity of the fragrance-containing substance 26 allows a relatively thick layer to be applied to the face 28 of the sheet 20, resulting in the concentration of a large amount of fragrant substance 26 onto a sheet having a relatively small net surface area This approach considerably extends the useful life of the air freshener without adversely affecting the flow characteristics of the HVAC system.

A suitable gel may be made by mixing the desired fragrant oil in a liquid petroleum distillate diluent. A gelling agent is dissolved in the mixture, creating a high viscosity liquid gel. The diluent increases the volume of fragrant liquid so as to increase the time required for evaporation, thereby extending the life of the fragrance. Such gels are available from Aroma Tech of Somerville, N.J. under the trademark "AromaGel." Present formulations have a useful fragrant life of up to about two weeks.

In a preferred embodiment of the invention, the fragrant gel 26 has a room temperature (23° C.) viscosity of approximately 3800 centipoise under an applied shear stress of 10 KPa. This allows the fragrance to be formed on the sheet 20 in a layer having a thickness of at least about 1/16 inch, so that at least about 0.06 cubic inches of fragrant gel 26 are applied for each square inch of the sheet covered by the fragrant gel. In one embodiment of the invention, this results in the production of an air freshener in which at least 23 grams of fragrant gel 26 are applied onto a square sheet 20, such as that shown in FIG. 3, that is about 6.5 inches long by 6.5 inches wide, and that has a net surface area—that is, excluding the surface area of the opening—that is no greater than about 36 square inches.

The fragrant gel 26 is applied by first heating it, preferably to approximately 260–280° F. This heating reduces the viscosity of the fragrant gel 26 sufficiently so that it can be sprayed or flowed on the sheet 20 in a variety of patterns, as previously discussed. Although the heated, reduced viscosity fragrant liquid initially begins to flow or spread out on the sheet upon application, its viscosity rapidly increases as it cools and gels. Natural cooling is preferably enhanced by a cooling medium, as discussed below, in order to reduce this initial flowing. As the fragrant liquid cools to room temperature, it adheres to the surface of the sheet 20 and its relatively high room temperature viscosity, discussed above, allows it to remain in place on the sheet as a thick layer during subsequent processing and handling, as well as in use. Thus, even when the device is oriented vertically, the layer of fragrant gel 26 does not run but maintains its geometric stability. As discussed above, the heating and subsequent cooling of the fragrant gel 26 are preferably controlled so as to result in a layer of fragrant gel that is at least about 1/16 inch.

Figure 8A:
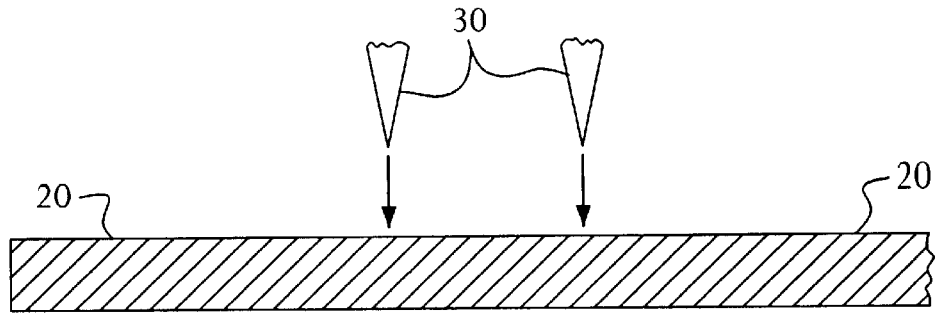
FIGS. 8a–d show cross-sections through the scenting device shown in FIG. 4 taken along line 8—8 during successive stages in the manufacturing process.
Figure 8B:
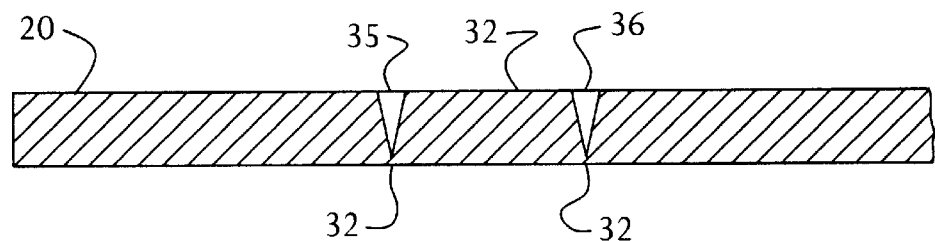

FIGS. 8a–d illustrate one method of making an air freshening device, such as that shown in FIG. 3, according to the current invention. First, a sheet 20 having the desired overall shape is formed from a suitable substrate material, such as blotter paper, as shown in FIG. 8a. The opening 22 is then partially die cut into the sheet 20, as shown in FIG. 8b. This is preferably accomplished by pressing knife blades 30, shown in FIG. 8a, through most, but not all, of the thickness of the sheet 20 so that a thin segment of material 32 remains intact and connects the cut-out portion 34 to the remainder of the sheet 20. The partial cuts create zones of weaknesses 35 and 36 in the sheet 20 that are shaped to correspond to the edges 21 and 23, respectively, of the opening 22. The zones of weaknesses 35 and 36 allow the sheet to be easily torn, as explained below. Preferably, the knife blades 30 have the same shape as the edges of the opening 22 so that the entire opening is cut in a single step.

Figure 8C:
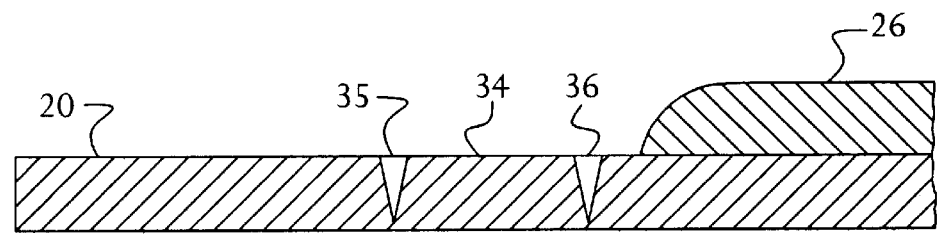

Next, the strip of fragrance containing gel 26 is deposited on the partially cut-through sheet 20, as shown in FIG. 8c. The fact that the sheet 20 is only partially cut through provides additional strength and rigidity to the sheet that it would not have had if the opening had been completely cut. This additional strength and rigidity allows more accurate placement of the strip of fragrance-containing gel 26. In addition, it ensures that gel does not flow through the opening 22 and foul the conveyor that transports the sheet 20 to the various stages of the manufacturing process.

After the gel 26 is applied, it is preferably cooled to reduce the set-up time and minimize the extent to which the material flows upon application to the sheet, as previously discussed. Preferably, the device is transported by conveyor through a cooling tunnel in which cooled air is directed over the gel to decrease cooling time. After cooling, the device is packaged in a foil pouch for shipment.

Figure 8D:
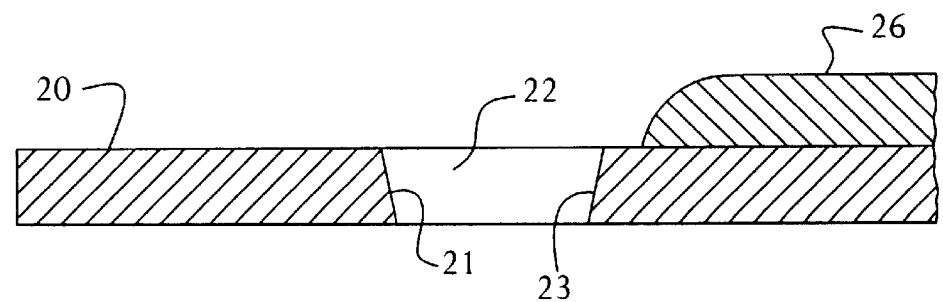

In the final step, the cut-out portion 34 is torn from the sheet 20, with the zones of weaknesses 35 and 36 ensuring that the tearing occurs through the portions 32, thereby creating an opening 22 having the desired shape, as shown in FIG. 8d. Preferably, the device is packaged and shipped to the user prior to performing the tearing step. Thus, the final step that forms the opening 22 in the sheet 20 is left to the person who applies the device to the air filter, such as a home-owner. Delaying the final formation of the opening 22 allows the manufacturer to take advantage of the additional strength and rigidity associated with a partially cut-through sheet during the packaging of the device.

The present invention may be embodied in other specific forms without departing from the spirit or essential attributes thereof and, accordingly, reference should be made to the appended claims, rather than to the foregoing specification, as indicating the scope of the invention.

What is claimed:

1. A scenting device for attachment to a filter through which air flows, comprising:
   a) a substrate, said substrate having first and second faces on opposing sides thereof, at least one air passage opening formed in said substrate said opening being serpentine in shape so as to define fingers in said substrate;
   b) a layer of fragrance-containing gel adhered to said substrate, said layer of fragrance-containing gel covering a portion of said substrate first face, said layer of fragrance-containing gel extending along said fingers, the room temperature viscosity of said fragrance-containing gel being sufficiently great so as to form a layer containing at least approximately 0.06 cubic inches of said fragrance-containing gel for each square inch of said portion of said first face covered by said gel layer; and
   c) a connector for attaching said sheet to said air filter so as to impart a desired scent to said air flowing therethrough.

2. The scenting device according to claim 1, wherein said substrate is formed from a material that is substantially impervious to air.

3. The scenting device according to claim 2, wherein said substrate is substantially planar and formed from blotter paper.

4. The scenting device according to claim 1, wherein said room temperature viscosity of said gel is at least approximately 3800 centipoise.

5. The scenting device according to claim 1, wherein only a single opening is formed in said substrate.

6. A scenting device for attachment to a filter through which air flows, comprising:
   a) a substrate, said substrate having first and second faces on opposing sides thereof, a zone of weakness formed in said substrate so as to allow a portion of said substrate to be torn therefrom so as to create at least one opening having a predetermined shape said zone of weakness being serpentine in shape so as to define fingers in said substrate;
   b) a layer of fragrance-containing gel adhered to said substrate, said layer of fragrance-containing gel covering a portion of said substrate first face, said layer of fragrance-containing gel extending along said fingers, the room temperature viscosity of said fragrance-containing gel being sufficiently great so as to form a layer containing at least approximately 0.06 cubic inches of said fragrance-containing gel for each square inch of said first face covered by said gel layer; and
   c) a connector for attaching said sheet to said air filter so as to impart a desired scent to said air flowing therethrough.

7. The scenting device according to claim 6, wherein said substrate is formed from a substance that is substantially impervious to air.

8. The scenting device according to claim 6, wherein said substrate is substantially planar and formed from blotter paper.

9. The scenting device according to claim 6, wherein said room temperature viscosity of said gel is at least approximately 3800 centipoise.

* * * * *

UNITED STATES PATENT AND TRADEMARK OFFICE
CERTIFICATE OF CORRECTION

PATENT NO. : 6,117,218
DATED : September 12, 2000
INVENTOR(S) : Snyder et al.

It is certified that error appears in the above-identified patent and that said Letters Patent is hereby corrected as shown below:

Column 2,
Line 39, please delete "formations" and insert therefor -- foraminous --.

Signed and Sealed this

Twenty-ninth Day of January, 2002

Attest:

JAMES E. ROGAN
Attesting Officer — Director of the United States Patent and Trademark Office